United States Patent [19]

Murphy, Jr. et al.

[11] 4,062,225
[45] Dec. 13, 1977

[54] ROTATIONAL VISCOMETER AND PLASTOMETER

[75] Inventors: Robert J. Murphy, Jr.; Dwayne E. Ortman, both of Houston, Tex.

[73] Assignee: NL Industries, Inc., New York, N.Y.

[21] Appl. No.: 716,719

[22] Filed: Aug. 23, 1976

[51] Int. Cl.² ............................................. G01N 11/14
[52] U.S. Cl. ........................................ 73/60; 318/313
[58] Field of Search ................ 73/60, 59, 54; 318/11, 318/313

[56] References Cited

U.S. PATENT DOCUMENTS

| 2,703,006 | 3/1955 | Savins | 73/59 |
| 3,435,666 | 4/1969 | Fann | 73/60 |
| 3,514,685 | 5/1970 | Burgess | 318/313 |
| 3,935,726 | 2/1976 | Heinz | 73/60 |

FOREIGN PATENT DOCUMENTS

| 1,245,183 | 9/1971 | United Kingdom | 318/313 |

*Primary Examiner*—Richard C. Queisser
*Assistant Examiner*—Joseph W. Roskos

[57] ABSTRACT

Concentric cylinder viscometer comprising means for rotating an outer sleeve which exerts a viscous drag on an inner cylinder, the torque of which is registered by spring means, and in which the outer sleeve is rotated at any of several pre-selected speeds by a direct current motor, the speed of which is controlled by a phase-locked feedback circuit in which the instantaneous speed of the motor is detected by an incremental encoder, the signal from which is fed to a digital display showing the rotational speed and is also fed back to the phase-locked comparator circuit which causes the application to the motor of the voltage required to drive it at the desired speed. The circuit includes an oscillator and frequency dividers which provide a plurality of precisely controlled frequencies, and also includes a variable oscillator which provides any desired hand-settable frequency over a wide range. The device is particularly adapted to the testing of drilling fluids.

3 Claims, 8 Drawing Figures

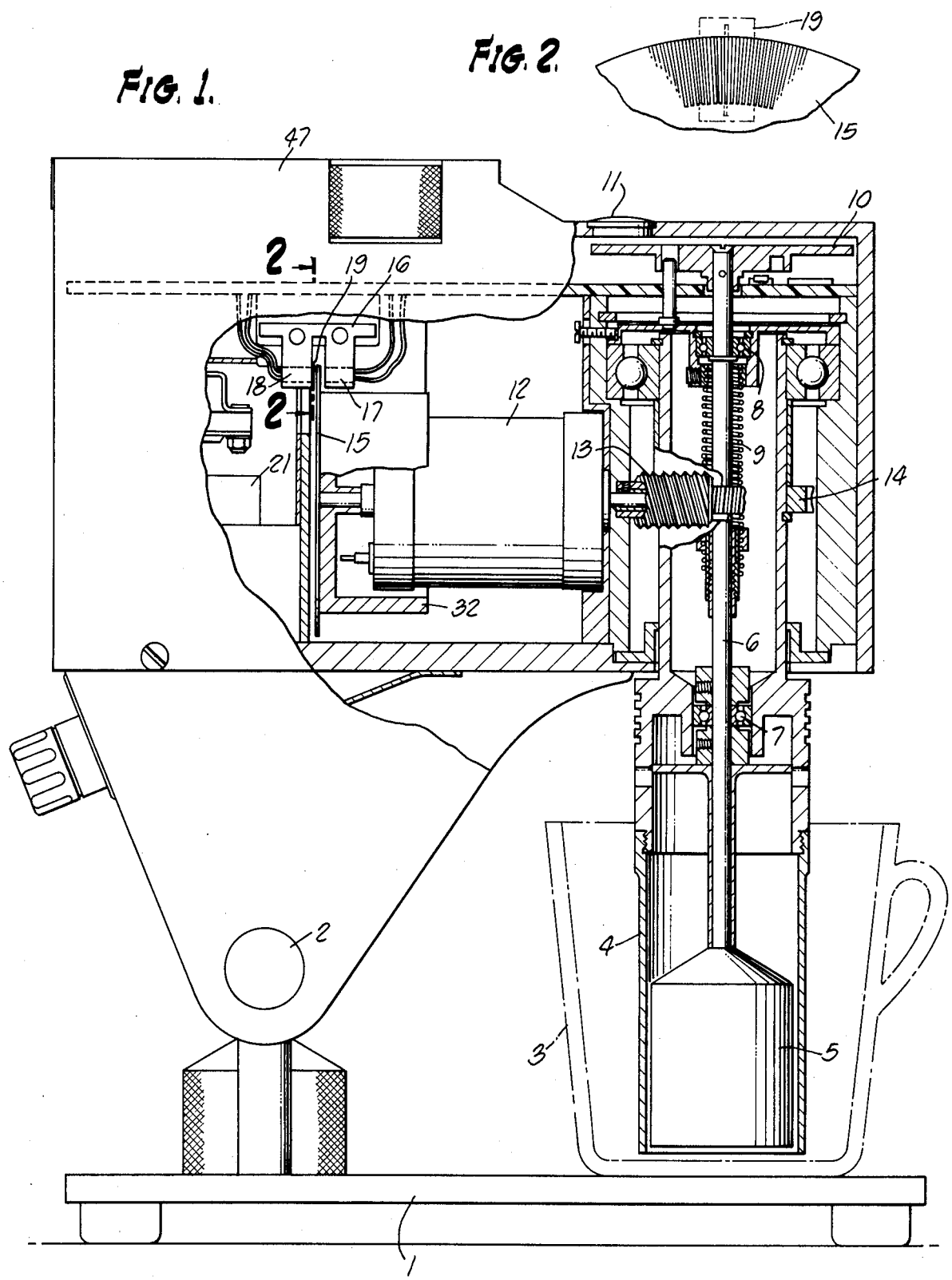

VARIABLE FREQUENCY OSCILLATOR

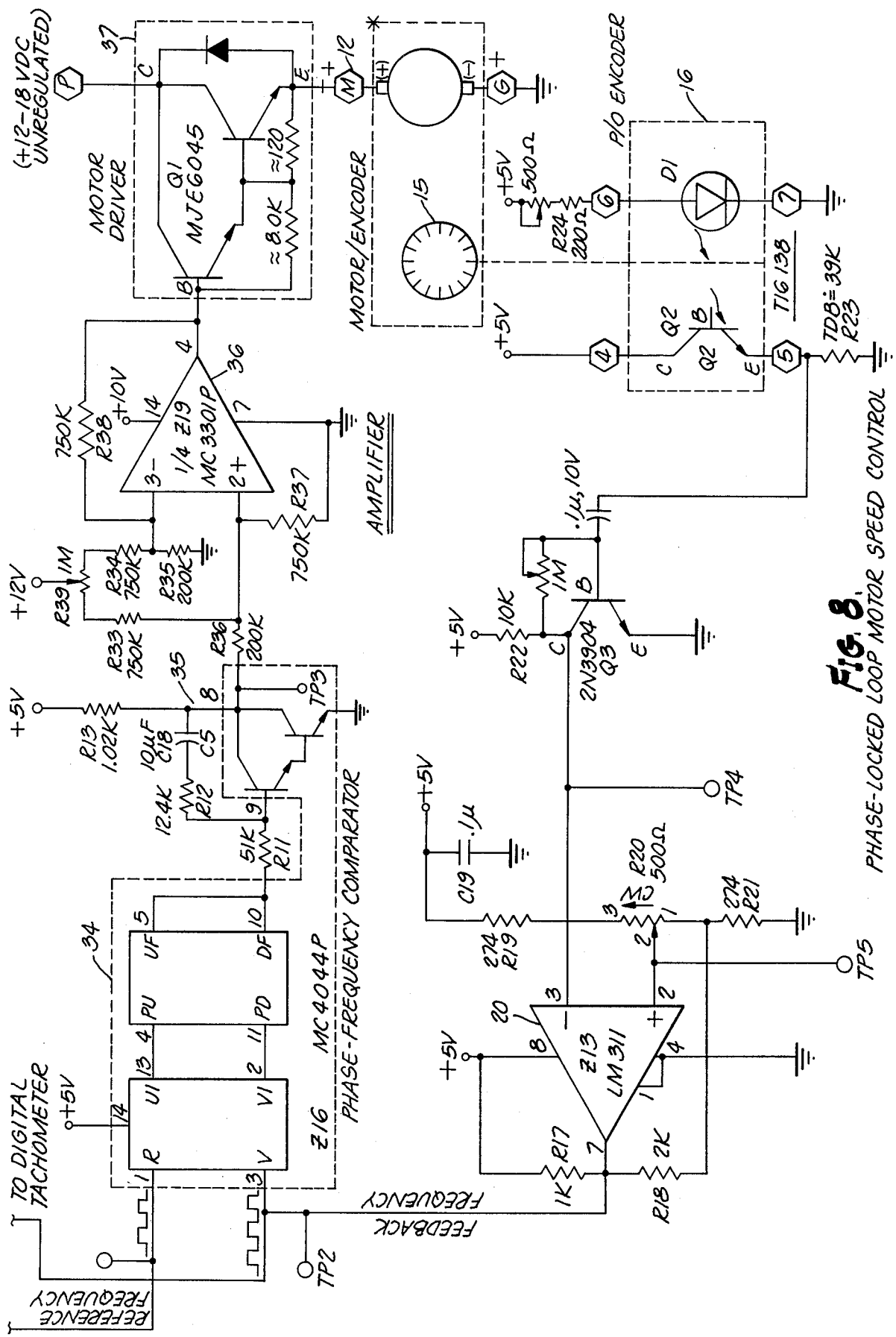

ROTATIONAL VISCOMETER AND PLASTOMETER

BACKGROUND OF THE INVENTION

This invention relates to concentric cylinder viscometers which are also plastometers, as used for determining the rheological characteristics of plastic and in particular thixotripic fluid, such as are used for example in petroleum well drilling and production, such as rotary drilling fluids, packer fluids, gravel and placement fluids, and hydraulic fracturing fluids.

Newtonian fluids such as most pure liquids of relatively low molecular weight undergo a finite shear when a finite shearing stress is applied, no matter how small the latter may be. For plastic fluids in general, there exists a shearing stress at and below which no shear takes place. Other fluids of intermediate character may have this limiting shear stress approach zero, but nevertheless exhibit a nonlinear relation between applied shearing stress and resulting shear. Some fluids which are not Newtonian may also exhibit a minimum shearing stress of the type described, that is, below which no shear takes place so that the fluid behaves essentially as a solid; and still other fluids may be of such a character that the minimum shearing stress increases with the time of quiescence.

It will be clear from the foregoing that fluids of the type described may be characterized by a number of parameters, and that these may have a considerable range of values. In the practical utilization of these fluids, accordingly, it is essential to be able to characterize a given fluid with respect to all of these parameters, and to do so in a reproducible and reliable fashion.

Some of the devices which have been used in various fields for the rheological characterization of non-Newtonian fluids are described in the text "Viscosity and Flow Measurement" by J. R. Van Wazer et al, Interscience Publishers, New York, 1963. Pages 156-161 of this text, hereby included herein by reference, relate to a type of concentric cylinder rheometer which has been widely used in applied petroleum technology, and which is described additionally in U.S. Pat. No. 2,703,006, to Savins.

SUMMARY OF THE INVENTION

An improved device of the general type described in the Savins patent and the Van Wazer text is provided in which rotational speeds are controlled with a high degree of accuracy, and torque is measured and indicated at a like degree of accuracy, all with no sacrifice in compactness and ease of operation.

DESCRIPTION OF THE DRAWINGS

In the drawings:

FIG. 1 is a side view, partly in section, showing our novel device.

FIG. 2 is a fragmentary plan view, taken as shown by the arrows in FIG. 1, of the chopping disc.

FIG. 8 is a circuit diagram of the phase-locked loop motor speed control.

DESCRIPTION OF THE SPECIFIC EMBODIMENT

Figure 3:
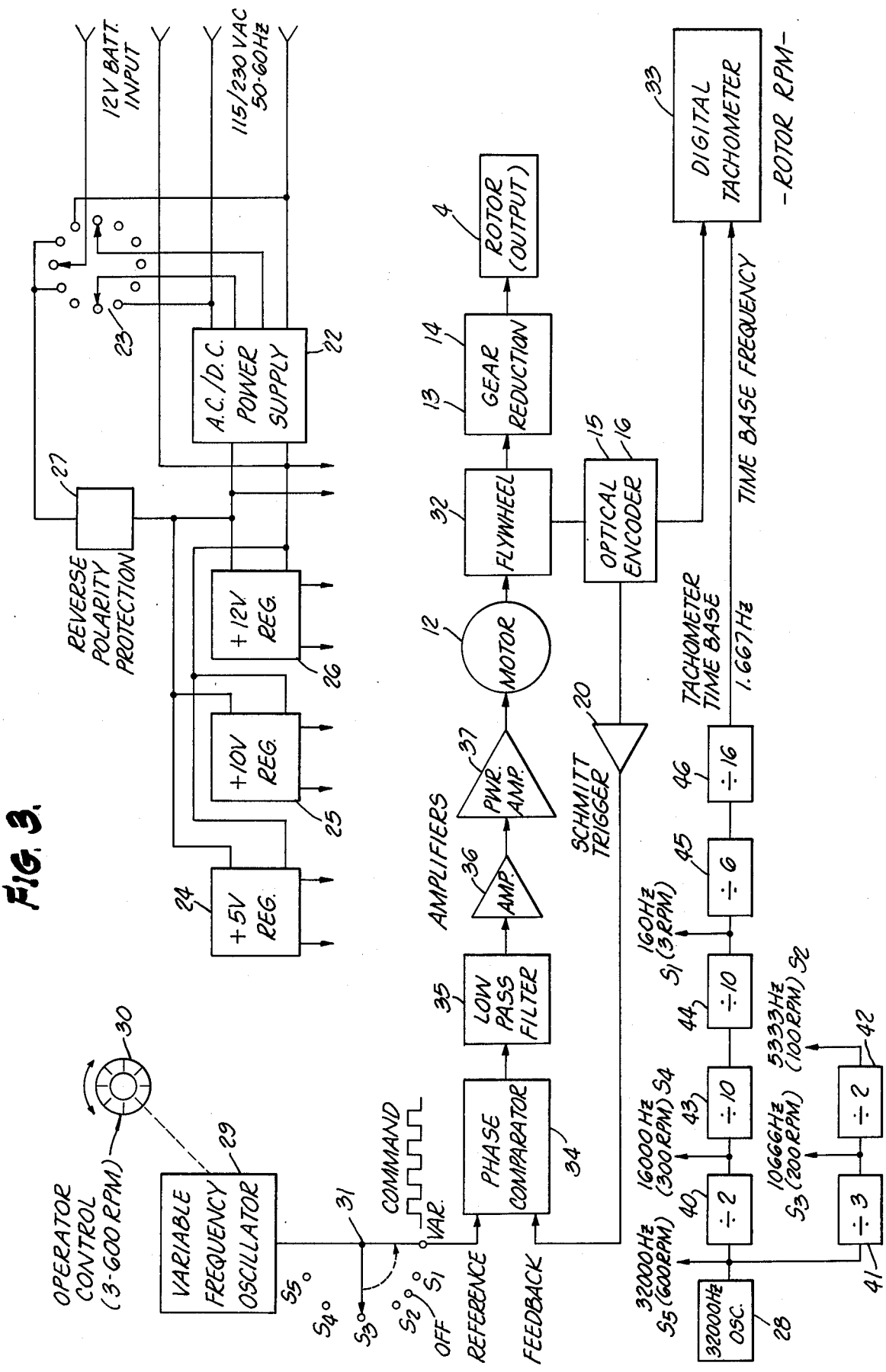
FIG. 3 is a block diagram showing the interrelationship of the electronic and associated mechanical components of the device.

Referring now to FIG. 1, 1 indicates a base plate to which the remainder of the apparatus is secured preferably by a pivotable joint 2, so that the rheometer may be swung upwards so as to enable the placing of a suitable vessel 3 filled with the fluid to be tested, after which the rheometer is returned to its normal position as shown in FIG. 1.

The primary sensing portion of our device comprises a rotatable cylindrical sleeve 4 within which is positioned an inner cylinder 5. When surrounded by fluid to be tested, the fluid fills the annular space between the inner cylinder 5 and the inside of the outer cylinder 4. When the latter is rotated, this annulus of fluid will tend to drag the inner cylinder along with it. While the inner cylinder is attached to a spindle 6 supported by ball bearings 7 and 8, rotation of the inner cylinder 5 in response to rotation of the sleeve 4 is restrained by the spring 9. Accordingly, under any given set of conditions of rotational speed of sleeve 4 and physical characteristics of the fluid to be tested and occupying the annular space between sleeve 4 and cylinder 5, the latter will rotate only far enough so that the spring 9 is rotationally tensed so as to counterbalance the torque exerted by the cylinder 5. The extent of rotation of the cylinder 5 may be observed by noting the deflection of the dial 10 which is attached at the top of the spindle 6 as shown in FIG. 1, this observation being facilitated by a magnifying lens 11 through which a scale engraved on the dial 10 may be observed.

The desired functions of our inventive device are the capability of rotating outer sleeve 4 at any of several pre-selected rotation rates; the ability to shift from one rotational rate to any other quickly and easily; the provision of a digital display which indicates the precise rotational speed of the sleeve 4 at all times; and the ability to determine the torque exerted on the inner cylinder 5 at any time. The last named characteristic has already been described. In the following detailed description the means which we have provided for accomplishing the remainder of the foregoing will be described.

While any set of pre-selected rotational speeds may be used, we have preferred to use those common in the drilling fluid testing art, which are 3, 100, 200, 300 and 600 revolutions per minute (rpm).

We have also provided a capability of hand setting the rotational speed of the outer sleeve 4 at any selected value between approximately 2 rpm and 650 rpm.

We provide a direct current motor 12 which drives sleeve 4 by means of a worm 13 which engages a worm gear 14 which is attached to the sleeve 4. The opposite end of the shaft of motor 12 carries an optical encoding disc 15, also known as a "chopping disc", a fragmentary plan view of which is shown in FIG. 2. The disc 15 is of transparent material, such as is used for photographic sheet film, and bears in its outer portion a series of radial black and transparent sectors. A portion of disc 15 which projects above the motor housing is straddled by an optoelectronic module 16, which is conveniently purchased as a complete unit, such as Texas Instruments type T1L138 source and sensor assembly. This comprises an infrared emitting diode in the location shown by 17, and a silicon phototransistor in the position shown by 18, in module 16. The light emitted by diode 17 passes through a narrow aperture in the mask 19 on its way to the sensor 18. The aperture in mask 19 is slightly narrower than the aperture spacing of the black and clear portions of disc 15, and is aligned therewith. Consequently, as disc 15 rotates, the light reaching sensor 18 is interrupted by the black lines on disc 15, giving rise to a quasi-sinusoidal signal transmitted by sensor 18 of the same frequency as that provided by the passage of the opaque lines across the mask. Schmitt-trigger 20 shapes this signal before it is sent to the phase-comparator and digital tachometer circuits.

The electronic circuits of our inventive rheometer are conveniently placed in the space indicated in FIG. 1 by 47, with the power supply transformer preferably where indicated by 21 in FIG. 1. These will now be described in greater detail.

Referring now to FIG. 3, which is a block diagram of the electrical and electronic circuits, we prefer to provide capability of operating the device from a 12 volt DC battery, or alternatively from alternating current of 50 to 60 Hertz and 115 or 230 volts. 22 in FIG. 3 indicates the unregulated DC power supply unit, with 23 being the power supply selector and on/off switch. 24, 25 and 26 provide 5 volts, 10 volts, and 12 volts respectively of regulated direct current where needed in the circuits. Circuit 27 provides reverse polarity protection and bypasses 12 volt regulator 26 during 12 volt DC battery operation.

We provide five fixed frequencies which are supplied by an oscillator 28 and frequency dividers 40, 41, 42, 43, and 44. We also provide a variable frequency oscillator 29 which may be hand set by the operator at any value corresponding to rotational speeds of 2 to 650 rpm, utilizing the knob 30. A switch 31 enables the switching into the circuit of any of the five fixed frequencies as well as the variable frequency from oscillator 29. The motor 12 is indicated in FIG. 3 with its flywheel 32 to which is attached the optical incremental encoding disc 15. The motor-flywheel combination drives the rotatable cylindrical sleeve 4 as already described.

The signal derived from the optical encoder 15, from the optoelectronic module 16, is sent through Schmitt-trigger 20 to the digital tachometer 33, which will be described later, and also, as may be seen from FIG. 3, to the phase comparator 34 which also receives the frequency signal selected by switch 31. From the phase comparator, the signal passes through the filter 35, amplifier 36, and power-amplifier 37, where it drives the motor at the desired speed.

The precise means whereby the motor is caused to run at precisely the selected speed, and whereby the actual motor speed is indicated at all times by the digital tachometer, will be made clear by taking the block diagram of FIG. 3 in connection with the circuit diagrams of the other Figures, which will now be described.

Figure 4:
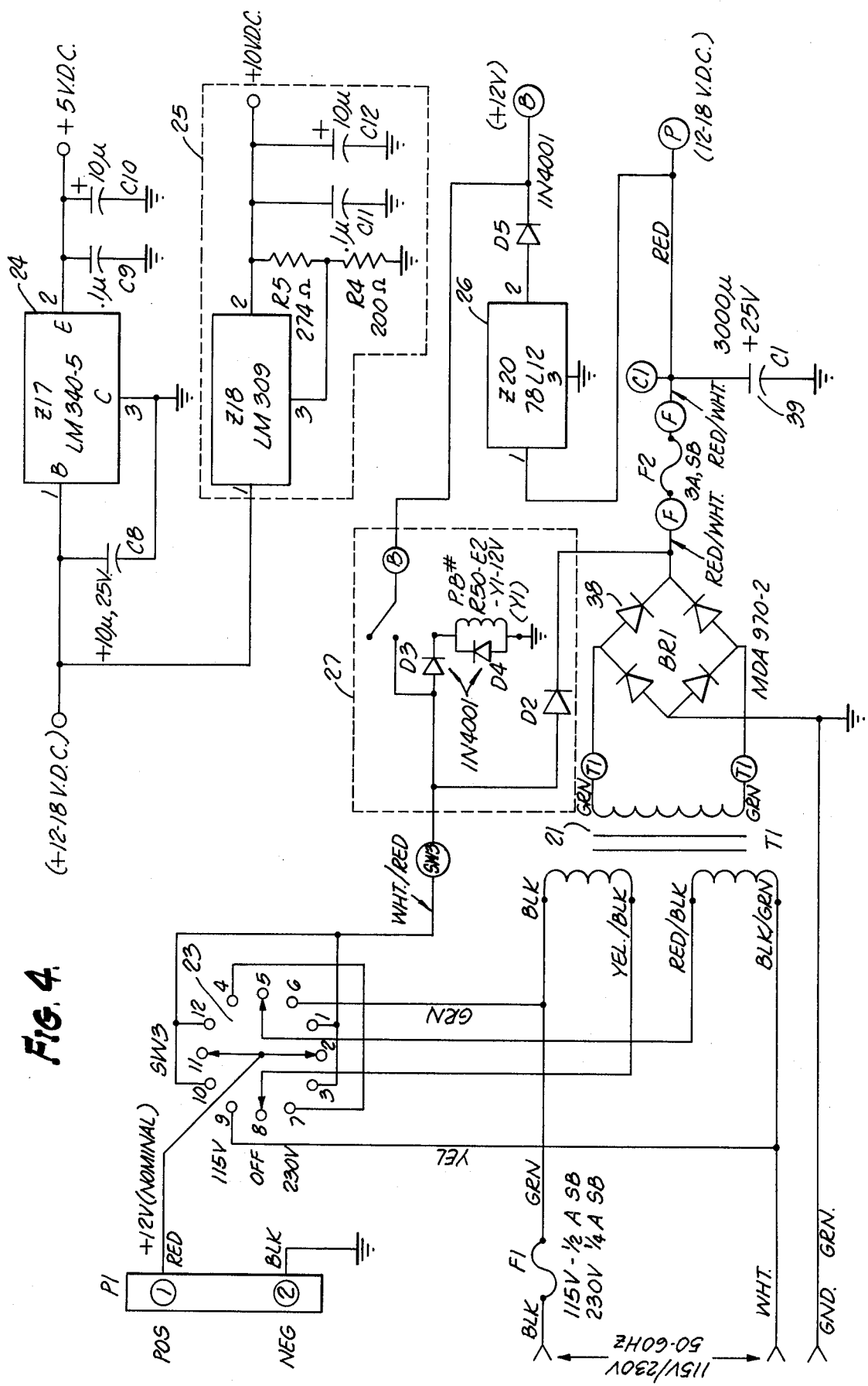
FIG. 4 is a schematic diagram showing the power supply.

Considering first FIG. 4, this shows the detail of power supply selector and on/off switch 23, power transformer 21, full wave bridge rectifier 38, and the filter capacitor 39 which provide 12-18 volts of unregulated direct current. Regulators 24, 25, and 26 provide 5 volts, 10 volts, and 12 volts, respectively, of regulated direct current to the various control and operating circuits as needed and as indicated in FIS. 5, 6, 7, and 8. Reverse polarity protection circuit 27 uses a relay and diode combination to provide protection and to bypass 12 volt regulator 26 during 12 volt battery operation.

Figure 5:
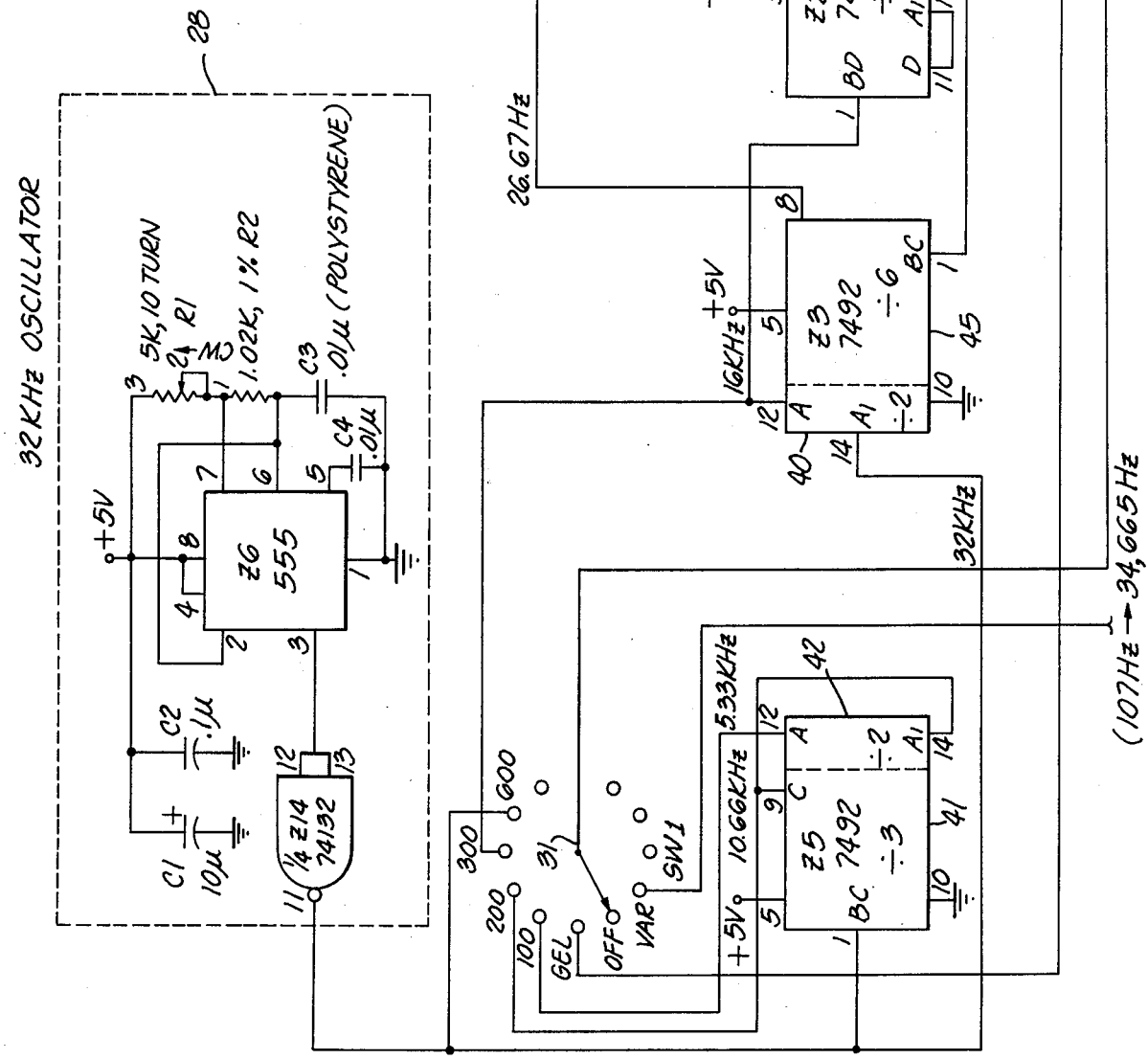
FIGS. 5 and 6 are circuit diagrams of the oscillator, counting and digital tachometer portions of the electronic circuitry.

Turning now to FIG. 5, this shows details of the fixed frequency oscillator 28, for which we prefer a frequency of 32 Kilohertz. This also shows details of the selector switch 31 and the frequency dividers 40, 41, 42, 43, 44, 45, and 46.

Figure 6:
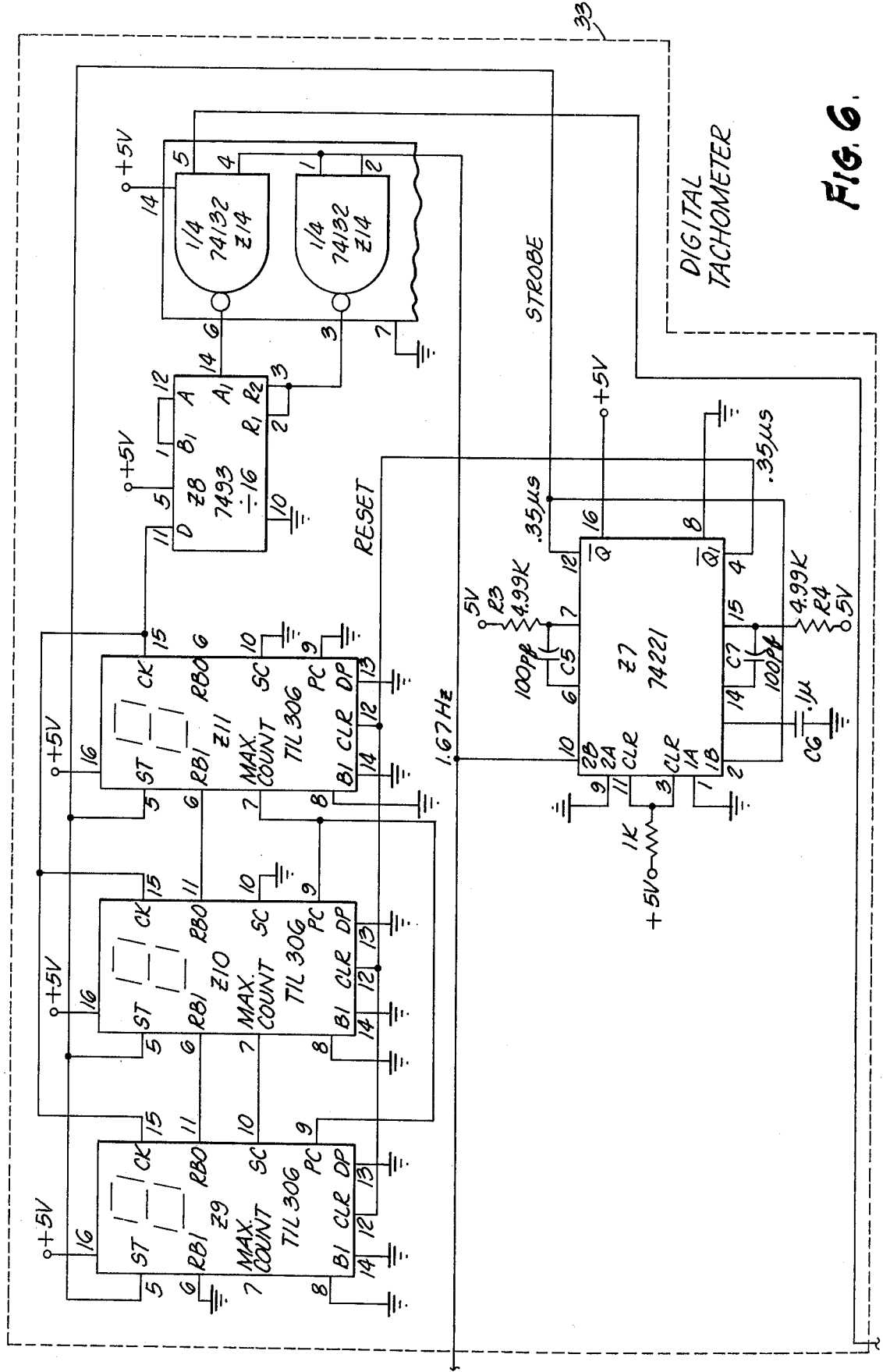
Figure 7:
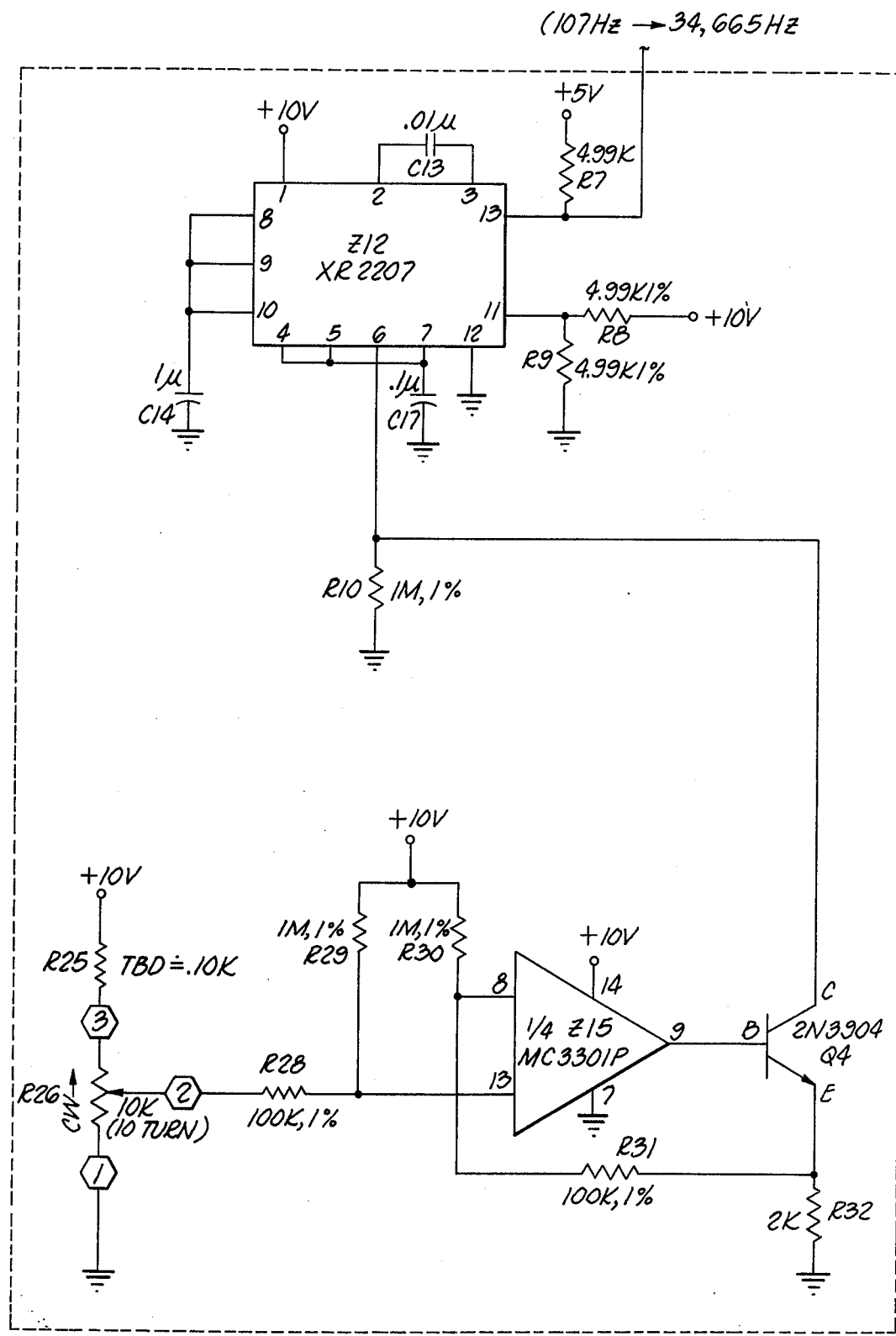
FIG. 7 is a circuit diagram of the variable frequency oscillator.

FIG. 6 shows details of the digital tachometer 33, while FIG. 7 shows details of the variable frequency oscillator 29.

FIG. 8 shows details of the phase comparator 34, the low pass filter 35, the amplifier 36, and the power or motor driving amplifier 37 driving the motor 12. It also shows details of the optical incremental encoder, 15, 16, and 20, which feeds its signal back to the phase comparator 34. These circuit diagrams of FIGS. 4–8 inclusive utilize the symbols and nomenclature common in circuit electronic technology, and will of course be readily comprehensible to those skilled in the art.

The motor 12 is a direct current motor, and we prefer a permanent magnet direct current motor for economy of space and cost. The speed at which such a motor runs is a function of applied voltage and load. By reason of the circuits which we have shown and utilize the voltage which is applied to motor 12 by amplifier 37 is automatically adjusted so as to be precisely the voltage necessary to drive the motor at the selected speed, with whatever load is presented to the motor by the rheological characteristics of the fluid being tested, which presents a frictional or viscous load since the liquid occupies the annular space between sleeve 4 and inner cylinder 5, as already explained. The speed at which the motor is running at any instant is detected by the optical encoder 15, 16, and 20, as already explained and fed back to phase comparator 34, which compares it with the frequency fed into the comparator by the switch 31. The remaining units 35, 36 and 37 act to supply exactly the necessary direct current voltage to the motor 12.

It will be appreciated that all of the components which have been described and which are recited in the claims cooperate to form an unusually effective working whole, viz, the inventive viscometer or rheometer as it may be styled. The demands placed upon the instrumentation by the working principle of this type of device, particularly when it is used in its preferred field of utility, that of rotary drilling fluids, are highly special. Thus, when any given fluid is tested at any selected rotational speed, the viscous drag between sleeve and cylinder remains substantially constant during the continued operation of the device. On the other hand, the viscous drags to be measured in practice vary over a wide range indeed, depending upon the viscosity, plastic viscosity, shear strength, thixotropic character, and other related rheological parameters which taken together make up the rheological character of the fluid. The device which we have described and claimed is especially well adapted to this demanding task, since it provides an accurate rotational speed which is maintained at the pre-selected value regardless of the viscous drag of the particular liquid tested, all resulting from the interrelationship of the sleeve, cylinder, motor means, rotational speed sensing means, oscillator means, and the electronic and other interconnections therebetween.

As those skilled in the art will recognize, the extreme low speed, e.g. 3 rpm, may be conveniently used for determining the shear strength of the fluid. Starting from rest, the sleeve drags the cylinder along with it, tensioning spring 9, until the fluid begins to undergo shear, at which point the torque can be visually observed.

The optical encoding disc 15 which we use in our preferred embodiment may of course be replaced by any number of alternative encoding means well known to those skilled in the art. Means other than optical may of course be employed in such devices, such as magnetic. All such devices, however, are encompassed by the term "incremental encoder" which we accordingly use herein and in the claim.

While we have described our invention with the aid of a detailed illustrative example, we wish it to be understood that we do not desire to be limited to the exact details of construction shown and described, for obvious modifications will occur to a person skilled in the art.

Having described the invention, we claim:

1. A concentric cylinder viscometer comprising, in combination, a cylindrical sleeve, means comprising a direct current motor for rotating said sleeve about its axis and means for rotating the sleeve at any of several pre-selected rotation rates; a cylinder disposed coaxially within said sleeve to provide an annular space betwen said sleeve and said cylinder; means for determining and registering the torque exerted on said cylinder upon rotating said sleeve when said annular space is occupied by a viscous fluid; incremental encoder means attached to said motor; means for deriving an electrical signal to said motor; means for deriving an electrical signal from said incremental encoder means indicative of the frequency of rotation of said motor; fixed frequency oscillator and divider means adapted to provide a plurality of pre-selectable frequencies; phase comparator means adapted to directly compare the encoder frequency to any of the oscillator frequencies; selector switch means for feeding any of said oscillator frequencies into said phase comparator; circuit connection means for feeding said electrical signal from said incremental encoder means into said phase comparator, and amplifier means operatively connected to said phase comparator adapted to provide a direct current voltage of sufficient magnitude to drive said motor at the speed determined by said pre-selected frequency.

2. Viscometer means in accordance with claim 1 comprising in addition variable oscillator means providing a pre-selected settable frequency.

3. Viscometer in accordance with claim 1 in which said electrical signal indicative of said rotational frequency is operatively connected with a digital tachometer supplying a digital readout of rpm, said meter deriving a time base from said fixed frequency oscillator.

* * * * *